United States Patent [19]

Modi

[11] Patent Number: 5,569,468

[45] Date of Patent: Oct. 29, 1996

[54] VACCINE DELIVERY SYSTEM FOR IMMUNIZATION, USING BIODEGRADABLE POLYMER MICROSPHERES

[76] Inventor: Pankaj Modi, 1928 Main St. W. Apt. 608, Hamilton, Canada, L8S 1J4

[21] Appl. No.: 197,754

[22] Filed: Feb. 17, 1994

[51] Int. Cl.$^6$ ............... A61K 9/64; A61K 9/58; A61K 9/60

[52] U.S. Cl. .......... 424/491; 424/488; 424/489; 424/490; 424/184.1; 424/493; 424/494; 424/495; 424/499; 514/963

[58] Field of Search ............... 424/184.1, 486, 424/488, 489, 490, 491, 493, 494, 495, 499; 514/963, 964, 965

[56] References Cited

U.S. PATENT DOCUMENTS

| | | | |
|---|---|---|---|
| 4,166,800 | 9/1979 | Fong | 427/212 |
| 4,272,398 | 6/1981 | Jaffe | 427/213.31 |
| 4,328,204 | 5/1982 | Wasserman et al. | 424/425 |
| 4,526,938 | 7/1985 | Chuchill et al. | 525/415 |
| 4,568,559 | 2/1986 | Nuwayser et al. | 427/2.15 |
| 4,622,244 | 11/1986 | Lapka et al. | 427/213.32 |
| 4,645,664 | 2/1987 | Lange | 514/772.7 |
| 4,675,189 | 6/1987 | Kent et al. | 424/490 |
| 4,755,397 | 7/1988 | Eden et al. | 427/213.3 |
| 4,832,686 | 5/1989 | Anderson | 604/49 |
| 4,897,267 | 1/1990 | Bontemps et al. | 424/422 |
| 4,904,479 | 2/1990 | Illum | 424/490 |
| 5,025,004 | 6/1991 | Wu et al. | 514/165 |
| 5,126,145 | 6/1992 | Evenstad et al. | 424/465 |
| 5,134,122 | 7/1992 | Orsolini | 514/15 |
| 5,187,150 | 2/1993 | Speiser et al. | 514/2 |
| 5,192,741 | 3/1993 | Orsolini et al. | 514/4 |
| 5,225,205 | 7/1993 | Orsolini | 424/489 |
| 5,417,982 | 5/1995 | Modi | 424/486 |

OTHER PUBLICATIONS

Eldridge et al. Molecular Immunology vol. 28, 287–294, 1991 Biodegradable Microspheres as a Vaccine Delivery System.

McKeating et al. J. Virology vol. 67, pp. 5216–5225, 1993 Resistance of Human Serum–Selected Human Immunodeficieny Virus Type 1 Escape Mutant to Neutralization By CD4 Binding Site Monoclonal Antibodies is Conferred by A Single Amino Acid Change in GP120.

*Primary Examiner*—Mary E. Mosher
*Assistant Examiner*—Lawrence J. Carroll, II
*Attorney, Agent, or Firm*—Robert E. Vernon

[57] ABSTRACT

A controlled release oral formulation, for human vaccines, are formed in microspherical form. The vaccine is suspended in a polymer matrix. The polymer matrix is formed from at least two highly water soluble biodegradable polymers, selected for example from starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyortho esters, polyetheneimine, polyethylene glycol, methoxypolyethylene glycol, ethoxypolyethylene glycol, polyethylene oxide,poly(1,3 bis(p-carboxyphenoxy) propane-cosebacic anhydride, N,N-diethylaminoacetate, block copolymers of polyoxyethylene and polyoxypropylene. The microspheres are coated with a (d,1 lactide-glycolide) copolymer. The coating makes the microspheres more resistant to enzymatic degradation.

28 Claims, No Drawings

VACCINE DELIVERY SYSTEM FOR IMMUNIZATION, USING BIODEGRADABLE POLYMER MICROSPHERES

TECHNICAL FIELD

The present invention relates to an improved delivery system for the administration of vaccines.

BACKGROUND

Extensive efforts have been expended on the identification of appropriate antigens for immunization against numerous infectious diseases. However, the efficiency of such vaccines often is low because of rapid degradation of antigens and their very short in-vivo half lives. The need for effective vaccination procedures is particularly acute with respect to organisms which produce their pathophysiologic effects through acute infections localized to the gastrointestinal surfaces. However, large doses have been required to achieve adequate local concentrations in the peyer's patches of the gastrointestinal tract. There is a need therefore to provide a vaccine delivery system which results in enhanced immunity without the need for adjuvants and is effective following oral administration. The present invention is intended to provide a delivery system which alleviates the aforementioned performance difficulties. The invention is suitable for injectable and oral vaccines, but oral administration is preferred. The vaccine is sometimes referred to herein as the antigen.

DICLOSURE OF INVENTION

Accordingly the present invention provides a controlled release formulation comprising biodegradable polymer microspheres wherein a vaccine is suspended in a polymer matrix, said polymer matrix being formed from at least two highly water soluble biodegradable polymers, and said microspheres being coated with a (d,1 lactide-glycolide) copolymer.

In one embodiment the polymers are selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyortho esters, polyethyleneimine, polyethylene glycol, methoxypolyethylene glycol, ethoxypolyethylene glycol, polyethylene oxide, poly(1,3 bis(p-carboxyphenoxy) propane-co-sebacic anhydride, N,N-diethylaminoacetate, block copolymers of polyoxyethylene and polyoxypropylene.

An example of a suitable polyortho ester is 3,9-bis(methylene)-2,4,8,10,-tetra oxaspiro[5,5]undecane/1,6 hexanediol poly (ortho ester).

It is preferred that the weight ratio of the two polymers is in the range of from 20:80 to 80:20.

In another embodiment the polymer matrix is selected from starch and ficoll, starch and polysucrose, starch and polyvinyl alcohol, starch and gelatine, hydroxyethyl cellulose and hydroxypropyl cellulose, gelatine and hydroxyethyl cellulose, gelatine and polyvinyl alcohol, polysucrose and polyvinyl alcohol, and sodium carboxymethyl cellulose and sodium alginate.

When the polymer matrix comprises starch and ficoll, the preferred weight ratio of starch to ficoll is preferably from 85:15 to 60:40, and more preferably from 75:25 to 65:35.

When the polymer matrix comprises starch and polyvinyl alcohol, the preferred weight ratio of starch to polyvinyl alcohol is in the range of from 35:65 to 65:35, with a more preferred range of from 40:60 to 60:40. A microsphere having a starch to polyvinyl alcohol of about 50:50 is suitable for release of active ingredient over about a 10 day period. The starch has a tendency to degrade relatively quickly and the polyvinyl alcohol tends to give to the microsphere, hardness and stability toward enzymatic and proteolytic degradation. Similar ratios are suitable for polysucrose and polyvinyl alcohol.

When the polymer matrix comprises one of the celluloses and ficoll, the preferred weight ratio of the cellulose to ficoll is in the range of from 80:20 to 65:35. Celluloses tend to give soft and stable microspheres.

The selection of the particular (d,1 lactide-glycolide) copolymer will depend in a large part on how long a period the microsphere is intended to release the active ingredient. For example, a (d,1 lactide-glycolide) copolymer made from about 80% lactic acid and 20% glycolic acid is very stable and would provide a microsphere suitable for release of active ingredient over a period of weeks. A (d,1 lactide-glycolide) copolymer made from 50% lactic acid and 50% glycolic acid is stable and would provide an microsphere suitable for release of active ingredient over a period of days. A (d,1 lactide-glycolide) copolymer made from 20% lactic acid and 80% glycolic acid disintegrates relatively easily and would provide an microsphere suitable for release of active ingredient over a period of 1–2 days. The coating makes the microspheres more resistant to enzymatic degradation.

In another embodiment, the antigen is selected from bacterial toxoids, cholera toxin B-subunit, influenza vaccine virus, *bordetela pertussis* vaccine, vaccinia virus, adenovirus, canary pox, polio vaccine virus, *Plasamodium falciparum, bacillus calmette* geurin (BCG), klebsiella pneumoniae and HIV envelope glycoproteins. Examples of bacterial toxoids are tetanus, diphtheria, pseudomonas A, *mycobacterium tuberculosis*. Examples of HIV envelop glycoproteins are gp 120 and gp 160 for AID vaccines.

The formulation is preferably in an oral form, although it may be in an injectable form.

The present invention also provides a process for making a controlled release formulation comprising microspheres of a vaccine suspended in a biodegradable polymer matrix polymer, said process comprising the steps of a) preparing an aqueous solution of at least two highly water soluble biodegradable polymers and adding thereto a vaccine antigen, b) mixing the solution and vaccine antigen with an emulsifying medium to form a homogenized microdroplet suspension, c) adding the homogenized microdroplet suspension slowly to a first organic solvent which contains a small concentration of a first surfactant, while stirring the microdroplet suspension and solvent, thus causing microspheres to precipitate, d) separating the microspheres from the first solvent and adding a solution of a (d,1 lactide-glycolide) copolymer in a second organic solvent which contains a small concentration of a second surfactant, and e) slowly evaporating the solvent, leaving behind coated microspheres.

Step b) may be accomplished at room temperature or less but temperatures of −5° C. to 10° C. are preferred with temperature in the range of from 0° C. to 5° C. being even more preferred. These temperature ranges are more suitable for the easy formation of the suspension.

The first organic solvent may be the same or different to the second organic solvent. A preferred first solvent is acetone and a preferred second solvent is an acetone and chloroform mixture.

Likewise the first surfactant may be the same or different to the second surfactant. Preferred surfactants are polyoxyethylene derivatives of fatty acid partial esters of sorbitol anhydrides, some of which are sold under the Tween trade mark. Preferred concentrations of surfactant are from 2 to 3% v/v of the solvent. At higher concentrations, the final microspheres tend to be irregular in shape.

In one embodiment the polymers are selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyortho esters, polyethyleneimine, polyethylene glycol, methoxypolyethylene glycol, ethoxypolyethylene glycol, polyethylene oxide, poly(1,3 bis(p-carboxyphenoxy) propane-co-sebacic anhydride, N,N-diethylaminoacetate, block copolymers of polyoxyethylene and polyoxypropylene.

It is preferred that the weight ratio of the two polymers is in the range of from 20:80 to 80:20, with a more preferred range of from 40:60 to 60:40.

When the polymer matrix comprises starch and ficoll, the preferred weight ratio of starch to ficoll is preferably from 85:15 to 60:40, and more preferably from 75:25 to 65:35.

When the polymer matrix comprises starch and polyvinyl alcohol, the preferred weight ratio of starch to polyvinyl alcohol is in the range of from 35:65 to 65:35, with a more preferred range of from 40:60 to 60:40. A microsphere having a starch to polyvinyl alcohol of about 50:50 is suitable for release of active ingredient over about a 10 day period. Similar ratios are suitable for polysucrose and polyvinyl alcohol.

When the polymer matrix comprises one of the celluloses and ficoll, the preferred weight ratio of the cellulose to ficoll is in the range of from 80:20 to 65:35.

In another embodiment the polymer matrix is selected from starch and ficoll, starch and polysucrose, starch and polyvinyl alcohol, starch and gelatine, hydroxyethyl cellulose and hydroxypropyl cellulose, gelatine and hydroxyethyl cellulose, gelatine and polyvinyl alcohol, polysucrose and polyvinyl alcohol, and sodium carboxymethyl cellulose and sodium alginate.

In another embodiment, the vaccine antigen is selected from bacterial toxoids, cholera toxin B-subunit, influenza vaccine virus, *bordetella pertussis* vaccine vaccinia virus, adenovirus, canary pox, polio vaccine virus, *plasmodium falciparum, bacillus calmette* geurin, *klebsiella pneumoniae* and HIV envelop glycoproteins.

In the first step of the process, the polymers which are intended to be used for the matrix are added to water, to form an aqueous solution, and the vaccine is added to the solution. This mixture is stirred and then mixed with an emulsifying medium, for example corn oil, rapeseed oil, vegetable oil. It is preferred that the amount of emulsifying medium exceed the amount of the polymer solution. For example, there may be as much as four times the amount of emulsifying medium as there is polymer solution. As indicated above, it is preferable that the mixture and emulsifying medium are held at a temperature lower than room temperature, and preferably between −5° C. and 10° C., especially from about 0° C. to about 5° C. The polymer, water, emulsifying medium and vaccine are stirred or otherwise mixed until a coarse pre-emulsion is formed. The pre-emulsion is further homogenized to form a microdroplet suspension, for example by high speed mixing. In the laboratory, such high speed mixing can be accomplished by sonication. In commercial manufacture, a high speed blender or turbine mixer is preferred. In the third step, the microdroplet suspension preferably is poured slowly into a large amount of organic solvent such as acetone, containing a small concentration of surfactant, e.g. about 2% v/v Tween® 80 surfactant, while stirring at high speed. Microspheres of the vaccine, drug or hormone in the polymer matrix precipitate. The purpose of the surfactant is to prevent agglomeration of the polymer matrix, with consequent loss of microsphere-sized particles.

The particle size of the precipitate is in the order of 100 nm to 100 μm, more typically in the 10 nm to 10 μm range.

In the fourth step, the microspheres are further coated with a (d,l lactide-glycolide) copolymer by transferring the microspheres into a solution of the copolymer in a second organic solvent which contains a second surfactant. For example, the microspheres may be added to a 2% solution of (d,l lactide-glycolide) copolymer in a 1:1 acetone/chloroform mixture which contains 1% v/v Tween® 80.

In the last step the second solvent and any remaining first solvent is removed by evaporation, so that a coating of (d,l lactide-glycolide) copolymer is left on the surface of the microspheres. A mild vacuum may be used to assist in the evaporation process.

The microspheres may then be made up in oral form or injectable form. The oral form is preferred. Clearly, the amounts and type of vaccine will depend on the immunizations required and the human being or animal being treated.

An advantage of the microencapsulation is that it increases the potency of weak antigens such as the small synthetic or recombinant peptides of HIV. Another advantage is that it enhances the speed, rigor and persistence of the immune response. A further advantage is that it modulates antibody avidity, specificity, quantity, isotype and subclass. Furthermore it decreases the amount of antigen needed to protect, thereby decreasing the cost and increasing the bioavailablility of the vaccines. Additionally, the microspherical form of the vaccine is more efficacious than an aqueous vaccine.

It will be understood by those skilled in the art that all of the ingredients must be suitable for ingestion by the animal or human. This means of course that toxic ingredients falling within the literal scope of the named chemical families mentioned herein would not be chosen.

The invention is illustrated by the following non-limiting examples.

EXAMPLE I 0.5 g starch was dissolved in 1 ml of dimethylsulphoxide (DMSO) and to this solution was added 0.5 g ethylhydroxycellulose and 0.1 g fluorescenated human serum albumine (FHSA) dissolved in 1 ml water. The solution was stirred to make a homogenous solution. To this solution was added 10 ml vegetable oil at 0° C. and the resulting mixture was sonicated to form a microdroplet suspension. The microdroplet suspension was added slowly to 200 ml acetone containing 2% v/v Tween® 80 surfactant. Microspheres were precipitated from the acetone. The acetone was decanted off and the microspheres were dried.

A 0.1 g sample of the microspheres was taken and the microspheres suspended in 3 ml of distilled water. This suspension was transferred to a UV cuvette. The absorbance of the FHSA at 390 nm wavelength was observed over a period of 90 days. The absorbance is indicative of the amount of FHSA released. The results are shown in Table I.

TABLE I

| Time (Days) | Absorbance |
| --- | --- |
| 1 | 0.18 |
| 2 | 0.21 |
| 3 | 0.40 |
| 7 | 0.45 |
| 11 | 0.61 |
| 30 | 0.77 |
| 60 | 1.10 |
| 90 | 1.85 |

Table I shows the slow release of the FHSA.

EXAMPLE II

The experiment of Example I was repeated except the flourescenated human serum albumine (FHSA) was replaced with myoglobin protein. The absorbance of myoglobin protein was monitored at 280 nm wavelength over a period of 120 days. The results are shown in Table II

TABLE II

| Time (Days) | % Myoglobin Released |
| --- | --- |
| 5 | 11 |
| 10 | 24 |
| 30 | 32 |
| 60 | 45 |
| 90 | 59 |
| 120 | 86 |

This shows the slow and steady release of the myoglobin protein.

EXAMPLE III

Human serum albumine (HSA) microspheres were made as in Example I except that the HSA was not fluorescenated. 50 mg of the microspheres were gavaged orally to Balb-C mice. The mice were bled at regular intervals and the blood samples centrifuged to isolate the plasma. The plasma was analyzed using ELISA techniques to estimate antibody titre (IgG) values. The results are shown in Table III.

TABLE III

| Time (Days) | Antibody titre (IgG) (Thousands) |
| --- | --- |
| 30 | 4 |
| 65 | 24 |
| 93 | 96 |

EXAMPLE IV

Human serum albumine (HSA) microspheres were made as in Example I except that the HSA was not fluorescenated and the hydroxyethyl cellulose was replaced by polyvinyl alcohol. 50 mg of the microspheres were gavaged orally to Balb-C mice. The mice were bled at regular intervals and the blood samples centrifuged to isolate the plasma. The plasma was analyzed using ELISA techniques to estimate antibody titre (IgG)values. The results are shown in Table IV.

TABLE IV

| Time (Days) | Antibody titre (IgG) (Thousands) |
| --- | --- |
| 30 | 6 |
| 65 | 13 |
| 93 | 98 |

I claim:

1. A controlled release formulation comprising biodegradable polymer microspheres wherein an antigen is suspended in a polymer matrix, said polymer matrix being formed from at least two highly water soluble biodegradable polymers, and said microspheres being coated with a (d,1 lactide-glycolide) copolymer.

2. A formulation according to claim 1 wherein the polymers are selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyethyleneimine, polyethylene glycol, methoxypolyethylene glycol, ethoxypolyethylene glycol, polyethylene oxide,poly(1,3 bis(p-carboxyphenoxy) propane-co-sebacic anhydride, N,N-diethylaminoacetate, block copolymers of polyoxyethylene and polyoxypropylene.

3. A formulation according to claim 1 wherein the weight ratio of the two polymers is in the range of from 20:80 to 80:20.

4. A formulation according to claim 3 wherein the polymer matrix is selected from the group consisting of starch and ficoll, starch and polysucrose, starch and polyvinyl alcohol, starch and gelatine, hydroxyethyl cellulose and hydroxypropyl cellulose, gelatine and hydroxyethyl cellulose, gelatine and polyvinyl alcohol, polysucrose and polyvinyl alcohol, and sodium carboxymethyl cellulose and sodium alginate.

5. A formulation according to claim 4 wherein the polymer matrix is starch and ficoll and the weight ratio of starch to ficoll is from 80:20 to 60:40.

6. A formulation according to claim 5 wherein the weight ratio is from 75:25 to 65:35.

7. A formulation according to claim 4 wherein the polymer matrix is starch and polyvinyl alcohol and the weight ratio of starch to polyvinyl alcohol is in the range of from 35:65 to 65:35.

8. A formulation according to claim 7 wherein the weight ratio is from 40:60 to 60:40.

9. A formulation according to claim 4 wherein the polymer matrix is polysucrose and polyvinyl alcohol and the weight ratio of polysucrose to polyvinyl alcohol is from 35:65 to 65:35.

10. A formulation according to claim 4 wherein the polymer matrix comprises ficoll and a member selected from the group consisting of hydroxymethyl cellulose, hydroxyethyl cellulose, hydroxypropyl cellulose, hydroxypropyl-ethyl cellulose, hydroxypropyl-methyl cellulose, sodium carboxymethyl cellulose and cellulose acetate and the weight ratio of the member to ficoll is in the range of 80:20 to 65:35.

11. A formulation according to claim 1 wherein the antigen is selected from the group consisting of bacterial toxoids, cholera toxin B-subunit, influenza vaccine virus, *Bordetella pertussis*, vaccinia virus, adenovirus, canary pox, polio vaccine virus, *plasmodium falciparum bacillus calmette* guerin, *klebsiella pneumoniae* and HIV envelope glycoproteins.

12. A formulation according to claim 2 wherein the antigen is selected from the group consisting of bacterial toxoids, cholera toxin B-subunit, influenza vaccine virus, *Bordetella pertussis*, vaccinia virus, adenovirus, canary pox, polio vaccine virus, *plasmodium falciparum bacillus calmette* guerin, *klebsiella pneumoniae* and HIV envelope glycoproteins.

13. A process for making a controlled release formulation comprising microspheres of an antigen suspended in a biodegradable polymer matrix polymer, said process comprising the steps of a) preparing an aqueous solution of at least two highly water soluble biodegradable polymers and adding thereto an antigen, b) mixing the solution and antigen with an emulsifying medium to form a homogenized microdroplet suspension, c) adding the homogenized microdroplet suspension slowly to a first organic solvent which contains a small concentration of a first surfactant, while stirring the microdroplet suspension and solvent, thus causing microspheres to precipitate, d) separating the microspheres from the first solvent and adding a solution of a (d,1 lactide-glycolide) copolymer in a second organic solvent which contains a small concentration of a second surfactant, and e) slowly evaporating the solvent, leaving behind coated microspheres.

14. A process according to claim 13 wherein the polymers used in step a) are selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyethyleneimine, polyethylene glycol, methoxypolyethylene glycol, ethoxypolyethylene glycol, polyethylene oxide,poly(1,3 bis(p-carboxyphenoxy) propane-co-sebacic anhydride, N,N-diethylaminoacetate, block copolymers of polyoxyethylene and polyoxypropylene.

15. A process according to claim 13 wherein the weight ratio of the two polymers used in step a) is in the range of from 20:80 to 80:20.

16. A process according to claim 15 wherein the polymer matrix is selected from the group consisting of starch and ficoll, starch and polysucrose, starch and polyvinyl alcohol, starch and gelatine, hydroxyethyl cellulose and hydroxypropyl cellulose, gelatine and hydroxyethyl cellulose, gelatine and polyvinyl alcohol, polysucrose and polyvinyl alcohol, and sodium carboxymethyl cellulose and sodium alginate.

17. A process according to claim 16 wherein the polymer matrix is starch and ficoll and the weight ratio of starch to ficoll is from 80:20 to 60:40.

18. A process according to claim 17 wherein the weight ratio is from 75:25 to 65:35.

19. A process according to claim 16 wherein the polymer matrix is starch and polyvinyl alcohol and the weight ratio of starch to polyvinyl alcohol is in the range of from 35:65 to 65:35.

20. A process according to claim 19 wherein the weight ratio is from 40:60 to 60:40.

21. A process according to claim 16 wherein the polymer matrix is polysucrose and polyvinyl alcohol and the weight ratio of polysucrose to polyvinyl alcohol is from 35:65 to 65:35.

22. A process according to claim 13 wherein the polymer matrix comprises ficoll and a member selected from the group consisting of hydroxymethyl cellulose, hydroxyethyl cellulose, hydroxypropyl cellulose, hydroxypropyl-ethyl cellulose, hydroxypropyl-methyl cellulose, sodium carboxymethyl cellulose and cellulose acetate and the weight ratio of the member to ficoll is in the range of 80:20 to 65:35.

23. A process according to claim 13 wherein the antigen is selected from the group consisting of bacterial toxoids, cholera toxin B-subunit, influenza vaccine virus, *Bordetella pertussis*, vaccinia virus, adenovirus, canary pox, polio vaccine virus, *plasmodium falciparum bacillus calmette* guerin *klebsiella pneumoniae* and HIV envelope glycoproteins.

24. A process according to claim 14 wherein the antigen is selected from the group consisting of bacterial toxoids, cholera toxin B-subunit, influenza vaccine virus, *Boretella pertussis*, vaccinia virus, adenovirus, canary pox, polio vaccine virus, *plasmodium falciparum bacillus calmette* guerin *klebsiella pneumoniae* and HIV envelope glycoproteins.

25. A method for immunizing animals and humans wherein a controlled release formulation is administered to the animal or human being, wherein the formulation comprises biodegradable polymer microspheres wherein an antigen is suspended in a polymer matrix, said polymer matrix being formed from at least two highly water soluble biodegradable polymers, and said microspheres being coated with a (d,1 lactide-glycolide) copolymer.

26. A method according to claim 25 wherein an antigen is administered to an animal or human being in the form of biodegradable polymer microspheres, said antigen being suspended in an a polymer matrix formed from at least two highly water soluble biodegradable polymers selected from the group consisting of polymer microspheres wherein the antigen is suspended in a polymer matrix, said polymer matrix being formed from at least two highly water soluble biodegradable polymers selected from the group consisting of starch, crosslinked starch, ficoll, polysucrose, polyvinyl alcohol, gelatine, hydroxymethyl cellulose, hydroxyethyl cellulose, hydroxypropyl cellulose, hydroxypropyl-ethyl cellulose, hydroxypropyl-methyl cellulose, sodium carboxymethyl cellulose, cellulose acetate, sodium alginate, polymaleic anhydride esters, polyethyleneimine, polyethylene glycol, methoxypolyethylene glycol, ethoxypolyethylene glycol, polyethylene oxide,poly(1,3 bis(p-carboxyphenoxy) propane-co-sebacic anhydride, N,N-diethylaminoacetate, block copolymers of polyoxyethylene and polyoxypropylene, and said microspheres being coated with a (d,1 lactide-glycolide) copolymer.

27. A method according to claim 25 wherein the formulation is administered orally.

28. A method according to claim 26 wherein the formulation is administered orally.

\* \* \* \* \*